United States Patent [19]

Kuhlmann et al.

[11] 4,299,977

[45] Nov. 10, 1981

[54] PREPARATION OF PHTHALIC ACID BY SOLVENTLESS OXIDATION OF LIQUID ORTHO-XYLENE

[75] Inventors: George E. Kuhlmann, Lisle; Alan G. Bemis, Naperville, both of Ill.

[73] Assignee: Standard Oil Company (Indiana), Chicago, Ill.

[21] Appl. No.: 867,050

[22] Filed: Jan. 5, 1978

[51] Int. Cl.³ ............................................ C07C 51/16
[52] U.S. Cl. .................................... 562/416; 562/412
[58] Field of Search ................... 260/524 R; 562/412, 562/416

[56] References Cited

U.S. PATENT DOCUMENTS

| | | | |
|---|---|---|---|
| 2,552,278 | 5/1951 | Hochwalt | 260/524 |
| 2,644,840 | 7/1953 | Roebuck | 260/524 |
| 2,858,334 | 10/1958 | Landau et al. | 260/524 |
| 3,920,735 | 11/1975 | Wampfler et al. | 260/524 |

Primary Examiner—Alan Siegel

Attorney, Agent, or Firm—Fred R. Ahlers; William H. Magidson; William T. McClain

[57] ABSTRACT

This invention relates to the preparation of o-phthalic acid by the oxidation of liquid o-xylene with a source of molecular oxygen at a temperature in the range of from 150° C. up to 235° C. in the presence of catalysis provided by the combination of components which include a source of bromine and at least cobalt as metal oxidation catalyst, in the presence of liquid water in an amount to activate said catalysis and solubilize a catalytically effective amount of metal oxidation catalyst in liquid phthalic acid and under conditions which retain substantially all the o-phthalic acid in the free acid form but in the absence of any material extraneous to the oxidation reaction or its products as solvent.

Such preparative process results in yields of 85 to 92 mole percent and higher to o-phthalic acid in but a single oxidation step with recycle thereto of only o-xylene vaporized from the reaction zone and recovered.

5 Claims, No Drawings

PREPARATION OF PHTHALIC ACID BY SOLVENTLESS OXIDATION OF LIQUID ORTHO-XYLENE

BACKGROUND OF THE INVENTION

The foregoing single step oxidation of liquid o-xylene is readily seen as superior to the oxidation of o-xylene vapor with air in the presence of solid particulates of vanadium oxide based catalyst which produces phthalic anhydride in 70 mole percent yield under non-explosive xylene to air concentrations and up to 78 mole percent yields with xylene to air concentrations well within the explosive range. Such oxidation of o-xylene in the vapor phase also results in the substantial over-oxidation of o-xylene to large amounts of oxides of carbon together with smaller amounts of maleic anhydride, citraconic acid and benzoic acid.

In contrast, in the conduct of the present invention the oxides of carbon produced amounts to 5 to 10 mole percent of the o-xylene but some of the oxides of carbon are from the co-production of 1 to 2 mole percent benzoic acid. Most of the o-xylene not so over oxidized, 3 to 7 mole percent, and not going to product appears as aromatic oxygen-containing co-products having boiling points well above the boiling temperature of o-phthalic acid and its anhydride.

U.S. Pat. Nos. 2,696,499 and 2,833,816 also describe a substantially solventless catalytic liquid phase oxidation of xylene at elevated temperature and pressure. The process of the first patent uses a xylene soluble cobalt compound (e.g., cobalt naphthenate, cumate, toluate, etc.) as catalyst and limits the oxidation to 10–50 percent conversion of xylene to toluic acid to suppress formation of unwanted oxygenated derivatives not precursors of phthalic acid. Such limited conversion also produces phthalic acid product which is separated (e.g., by filtration) and the filtrate is distilled to remove precursors of toluic and phthalic acids and reject the unwanted non-precursors. Said precursors are returned to the oxidation with fresh xylene and catalyst.

The second patent uses a polyvalent metal (e.g., cobalt, manganese or mixture thereof) with a source of bromine as the catalyst. Such xylene oxidation results in a 20–30% conversion of the xylene to phthalic acid product and the remainder to mainly toluic acid. The phthalic acid product is separated from toluic acid which is added to fresh xylene and catalyst and charged to the oxidation step.

U.S. Pat. No. 3,920,735 describes a solventless air oxidation of o-xylene at 205° C. and gauge pressure of 21 kg/cm$^2$ using for each gram mole of xylene 3 milligram atoms of each of cobalt, manganese and zirconium and 9 milligram atoms of bromine from hydrogen bromide. The reaction product comprised the following products in the molar yields based on the o-xylene charged: phthalic anhydride, 61 mole %; o-toluic acid, 0.97 mole %; phthalide, 3.95 mole %; 2-carboxybenzaldehyde, 1.88 mole %; and 0.1 mole % o-xylene. Also 10.5 mole percent of the o-xylene was burned to oxides of carbon and water.

The prior solventless catalytic liquid phase oxidation of o-xylene closest to the present inventive liquid phase oxidation is disclosed in British Pat. No. 856,245 published Dec. 14, 1960. Such solventless process was conducted at a temperature of 150° C. in the presence of a mixture of cobalt and maganese bromides as catalyst, at atmospheric pressure, and in an apparatus equipped with a water removal decanter. But said oxidation ceased when 70 mole percent of the o-xylene had been converted to phthalic anhydride. However, the 30 mole percent partially oxidized products when combined with both fresh o-xylene and catalyst is reported as proceeding upon further oxidation only to a tar-like product rather than to phthalic anhydride. It is further reported in said British Patent that small quantities of such tar-like product when added to a large quantity of o-xylene would inhibit its oxidation.

To overcome such limitations on solventless oxidation of o-xylene the patentee of the British Patent devised a two step oxidation wherein the first step is conducted in the presence of catalysis provided by only a polyvalent metal oxidation catalyst (i.e., no or very low ratio of bromine to xylene) until oxygen consumption ceases; and the second step is conducted also until oxygen consumption ceases in the presence of catalysis provided by both the polyvalent metal oxidation catalyst and a source of bromine with the product of the first step free or freed of unchanged o-xylene. Such process is illustrated by use of 20 hour reactions in each of the two steps conducted at a temperature of 150° C., at atmospheric pressure and in apparatus equipped with a water removal decanter. By such 40 hours of reaction and without recycle of intermediate oxygenated products, phthalic anhydride was produced in a 40 mole percent yield and 98.8% purity.

The present inventive process not only avoids the formation of oxidation inhibiting tar-like co-products but also in a single oxidation step without recycle of precursor intermediate oxidation products can produce 85 to 95 mole percent yields of impure o-phthalic acid readily converted to partially purified phthalic anhydride of 98% purity.

Such results are indeed suprising in view of the fact that the present inventive one step oxidation uses both the polyvalent metal oxidation catalyst and bromine in an amount substantially greater than used in the first step of the two step process of the British Patent.

SUMMARY OF THE INVENTION

The features of the present inventive one step oxidation of o-xylene which produce such surprising results are (1) maintaining a catalytically effective amount of the metal component of catalysis in a form soluble in o-xylene and the liquid reaction mixture and (2) maintaining the dicarboxy benzene product as substantially only the free o-phthalic acid at the operating oxidation temperature.

The first essential condition: maintaining a catalytically effective amount of the metal component of catalysis dissolved in o-xylene and the reaction mixture at the oxidation temperature range of 150° up to 235° C., has two different requirements. The first requirement of solubilizing the catalyst metal components in o-xylene is accomplished by providing one equivalent of o-xylene soluble aromatic monocarboxylic acid preferably benzoic or o-toluic acid, per equivalent of catalyst metal component present. Catalysis activity requires the presence of free liquid water in an amount of at least two weight percent of the reaction mixture. But catalytic activity becomes sluggish when water concentration in the reaction mixture exceeds seven weight percent and substantially cease when the water concentration is eight weight percent and above. The second requirement of solubilizing the metal components of catalysis in the reaction mixture must be considered from the standpoint of such solubility in liquid o-phthalic acid which is the main component, 80–96 weight percent, of the final reaction mixture. Fortunately catalytically effective amounts of the metal components of catalysis are soluble in liquid o-phthlaic acid containing from 2 to 7 weight percent liquid water at temperatures of from 185° C. (melting point of o-phthalic acid containing 7 wt. % water) up to 197° C. (melting point of o-phthalic acid containing 2 wt. % water) at the operating pressures of from 17.6 kg/cm² up to 28 kg/cm² gauge pressure.

Said 17.6 kg/cm² to 28 kg/cm² operating gauge pressure is required not to maintain a liquid phase of o-xylene or o-phthalic acid at the oxidation operating temperature of 150° up to 235° C. Rather said operating gauge pressure range is set by the effect of pressure on the dehydration of o-phthalic acid to its anhydride at temperatures in the range of 150° up to 235° C. Again the presence of the 2–7 weight percent water is fortunate because it plays yet a third role, that of assisting the retarding of said dehydration.

The foregoing essential conditions have two different technical effects. The first technical effect is the provision of catalysis to carry the oxidation well beyond the mid-point, that is, well beyond the formation of substantially only o-toluic acid by preventing the formation of oxidation inhibiting and/or limiting co- and/or by-products. The second technical effect is the provision of active catalysis to the very end of the oxidation, that is, a catalysis so active throughout the reaction that the presence of partial oxidation product impurities: 2-carboxybenzaldehyde, o-toluic acid and phthalide, are substantially eliminated. This latter feature is dependent upon keeping o-phthalic acid product substantially only in the free acid form. Otherwise, as we have discovered, in the course of o-phthalic acid dehydrating to its anhydride a metal-containing composition forms from the metal component of catalysis and the dehydrating o-dicarboxylic acid. Such metal-containing composition once formed cannot under the reaction conditions be treated in any feasible manner to bring about release of the catalyst metal. Thus once said dehydration-metal trapping condition occurs, the catalyst metal component of catalysis becomes irretrievably lost for catalysis and the oxidation ceases.

The foregoing essential conditions are applicable for catalysis supplied by from 0.3 up to 10 milligram atoms ("mga") of cobalt per gram mole of o-xylene ("gmx") provided however when said cobalt to o-xylene ratio is less than from 0.75 mga to 1.0 down to 0.3 mga to 1.0 the mga/gmol difference is made up by the use of non-polyvalent zirconium in a mga/gmx amount of from 0.2 up to 0.45 mga Zr per gmx. With such use of cobalt or cobalt and zirconium there are also used from 0.5 to 2 mga manganese per mga of cobalt or total of cobalt and zirconium to suppress excessive total combustion of o-xylene caused by cobalt. The bromine component of catalysis is at least 0.5 but less than 2.0 mga of bromine per mga of total metals.

The source of bromine is not important with respect to this component of catalysis in the generally applicable inventive concept of the present invention. Thus within the art recognized (from U.S. Pat. No. 2,833,816) unique catalysis from the combination of a source of bromine and one or more polyvalent metal oxidation catalysts, such bromine component can be from such sources as organic (e.g., tetrabromoethane, bromoacetic acid or benzylbromide), inorganic (e.g., sodium, or ammonium or hydrogen bromide) or elemental ($Br_2$) bromine. However, the source of bromine does become important with respect to the type of total process design, economics of the process and ultimate form of o-phthalic acid marketed. For example, for a total process which includes the steps of o-xylene oxidation to a liquid product containing mainly o-phthalic acid, recovery of phthalic acid or its anhydride from such liquid product, and recovery of components of catalysis for their recycle to and reuse in the oxidation step, the source of bromine can be hydrogen or ammonium bromide but not alkali or alkaline earth metal bromides because their use and such recycle use tends to cause accumulation of such metals in the oxidation and adversely effect its course and rate. The amount of o-xylene consumed by total combustion to oxides of carbon and water is a matter of concern to the economics of the process. The use of elemental bromine or bromocarboxylic acids (e.g., bromoacetic) appear to be the only bromine sources having a retarding effect on such total combustion of o-xylene. The use of organic bromides (e.g., tetrabromoethane) as source of bromine for the oxidation catalysis results in a rather dark colored liquid reaction product. This is only of importance when the o-phthalic acid so produced is converted to and recovered as its anhydride as the marketed product because the dark colored is difficult to remove and carries over to the anhydride. But when the darkly colored o-phthalic acid or its colored anhydride are esterified with mono-hydroxy alkanols (e.g., methyl to octyl alcohols), the resulting ester products which are normally liquid can be readily purified and decolored by conventional methods to meet the commercial color standards set for such esters.

Thus when the present inventive solventless oxidation of liquid o-xylene is conducted as part of a total process for the production of marketable phthalic anhydride the preferred source of the bromine component of the catalysis is elemental bromine and hydrogen bromide.

The operating temperature range of the present inventive solventless process has been indicated as from 150° C. up to 235° C. The final liquid reaction product can contain from 80 up to 95 weight percent o-phthalic acid. The 231° C. melting point temperature of pure o-phthalic acid is lowered by the presence of 2 to 7 weight percent water to, respectively 197° C. and 185° C. The presence of oxygen-containing aromatic co- and by-products further depresses the melting point of the final liquid reaction mixture. But generally the final reaction mixture does not have a melting point below 170° C. However, the starting mixture of o-xylene catalyst components and their solubilizers water and o-toluic acid or benzoic acid is liquid at a temperature below 150° C. and the oxidation of o-xylene will initiate at a temperature of 150° C. at the upper portion of the cobalt to xylene ratio range. Also the reaction mixture remains liquid at a temperature of 150° C. well beyond the conversion of o-xylene to o-toluic acid (M.P. 107°–108° C.). Total combustion of o-xylene and some of the first formed oxygenated products before all the o-xylene has been converted to o-toluic acid is enhanced as operating temperature is increased. Thus it is expedient to initiate the oxidation at a temperature of from 150° to 160° C. and permit the exothermic reaction to increase the reaction temperature to not more than 235° C., preferably in the range of 205° to 230° C. for an average operating temperature in the range of from 200° to 228° C. until the reaction is complete. Such conduct of the oxidation can be carried out with air supplied to provide, on a water and xylene free basis, an exhaust having from 2 up to 15, preferably 4 to 6, volume percent oxygen.

The catalytic liquid phase oxidations of xylene conducted in the presence of acetic acid or propionic acid solvent in an amount of from 2 to 10 weight parts per weight part of xylene can make use of heat of reaction to boil said alkanoic acid solvent. By condensing the acid solvent vapors the heat of reaction is effectively removed and temperature control achieved. The acid solvent condensate is returned to the reaction zone to minimize the amount of acid solvent used for such heat removal.

However, in the present catalytic liquid phase solventless process of oxidizing o-xylene to o-phthalic acid there is either nothing present for the heat of reaction to boil at the operating pressure or the amount of a substance present that does boil is so small that such boil up is insignificant with respect to the total amount of heat of reaction to be removed. Thus for the present inventive process heat of reaction is removed by indirect heat exchange between the liquid in the oxidation zone and a cooling liquid which does not thermally decompose at a temperature in the range of from 240° C. up to 350° C. Any suitable indirect heat exchange means, for example a cooling jacket which is an integral part of the oxidation reactor; an internal cooling coil; or internal cooling tubes being suitably interconnected by inlet and outlet manifolds for the flow therethrough of cooling liquid; or an external heat exchange such as a tube and shell heat exchanger.

There remains for the conduct of the present inventive process the control of water content of the reaction mixture within the 2 to 7 weight percent range. This involves removing by-product water from the oxidation zone. The ultimate goal of control of water content in the oxidation zone is to keep the metal components of the catalysis dissolved in the reaction medium as it changes from o-xylene to liquid o-phthalic acid. To just maintain the same water concentration throughout the oxidation some of the by-product water must be retained in the oxidation zone because the aromatic components in the reaction zone increase in weight as the oxidation progresses. A convenient way to remove some of the by-product water is to convey the gaseous mixture from the oxidation zone through a partial condenser and then through a total condenser. By operation of the partial condenser as a reflux condenser within the temperature and gauge pressure range of from 110° C. and 17.6 kg/cm² up to 138° C. and 28.1 kg/cm² where the oxidation zone operating pressure is within the same gauge pressure range. Operation of the reflux partial condenser under said temperature-pressure conditions will permit removal of at least 75% and retention of not more than 25% of the by-product water in the oxidation zone. For example, by operation of the reflux partial condenser at a selected temperature within said temperature-pressure range the initially charged water can be 2 weight percent of the o-xylene charged and the water concentration in the final reaction mixture upon completion of the o-xylene oxidation will not exceed 7 weight percent by accumulation by-product water in the oxidation zone.

Such selection of reflux partial condenser operating temperature can be made while conducting the solventless oxidation at a gauge pressure within the range of 17.6 to 28.1 kg/cm² provided that the supply of oxygen (e.g., air) to the oxidation exceeds its consumption as indicated by unused oxygen in the exhaust gas. From the stoichiometry of the reaction a plot of theoretical amount of by-product water per minute v net oxygen consumption per minute can be made before starting the reaction. Thus by supplying the oxygen at a fixed rate, measuring the flow of exhaust and analyzing it for its oxygen content the net oxygen consumption per minute can be ascertained for use with said plot to find the by-product water produced per minute. By collecting the water condensed by the total condenser and comparing the rate of such collection to the theoretical rate of by-product water production will indicate whether and at what rate by-product water is being accumulated in the oxidation zone. In the event by-product water is determined as being accumulated too rapidly in the oxidation zone, the first selected operating temperature of the reflux condenser is too low and needs to be adjusted upwardly. When it is determined that by-product water is being accumulated too slowly, the reflux condenser's operating temperature needs to be decreased. There is sufficient time during the operation of the present inventive solventless o-xylene oxidation under the preferred operating conditions to make such determinations and adjustments because at those conditions the oxidation reaction is substantially complete in from 60 to 90 minutes.

The use of air or air fortified with oxygen gas to supply the molecular oxygen reactant provides a spent air (mixture of nitrogen, oxides of carbon and unconsumed oxygen) of 2–5 volume percent oxygen. Such spent air leaving the liquid phase reaction mixture also carries vapors of by-product water and o-xylene, out of the reaction zone as its exhaust. Such exhaust also contains a mist-form of o-xylene. The vapor form of o-xylene in the exhaust from the reaction zone is readily condensed by the hot reflux condenser operated under a gauge pressure of from 17.6 up to 28.1 kg/cm² gauge pressure and a temperaure of from 110° up to 138° C. But the mist-form of o-xylene passes through such condenser entrained in the spent air containing the uncondensed water vapor and even through the total condenser unless some demisting means is incorporated in the total condenser. By the use of such combination of reflux partial condenser, total condenser and its demister substantially all, at least 98%, of the o-xylene as vapors and mist leaving the oxidation zone can be separated from the spent air and returned to the oxidation zone.

PREFERRED OPERATING CONDITIONS

Preferably the operation of the present invention solventless oxidation of o-xylene is conducted within the temperature range of from 200° C. up to 230° C.; under a gauge pressure of 28 kg/cm²; in the presence of from 0.75 up to 1.0 milligram atom of cobalt, from 1.5 up to 2.0 milligram atoms of manganese and from 2.25 up to 3.0 milligram atoms of bromine per gram mole of o-xylene; from 0.1 up to 0.2 gram mole of o-toluic acid or benzoic acid per gram mole of o-xylene; and from 3 to 5 weight percent water in the reaction mixture. Such operation of the present inventive process conveniently provides substantially complete conversion of o-xylene in the reaction mixture in from 60 to 100 minutes at an average air input rate of from 5 to 6 normal liters of air per minute per liter of o-xylene charged at which rate the inlet temperature of the reflux partial condenser needs to be in the range of from 118° to 140° C.

It will be noted that the preferred 0.1–0.2 gram mole of o-toluic acid or benzoic acid per gram mole of o-xylene is substantially greater than the 4.5 to 6 milli equivalents required to solubilize the preferred 2.25 to 3 milligram atoms (4.5–6 milli equivalents) total of catalyst metal. The excess of benzoic acid over such metal catalyst solubilizing need is preferred because such excess supresses total combustion of o-xylene to oxides of carbon and water. The use of a similar or even greater excess of o-toluic acid does not as effectively suppress total combustion of o-xylene because the o-toluic acid content of the reaction mixture decreases by oxidation to o-phthalic acid rather than remaining substantially unchanged as benzoic acid does.

The following illustrative and comparative examples are presented to establish the critical nature of the limits of the general operating conditions of the present inventive process and to demonstrate the benefits of the preferred operating conditions.

The following two oxidations of o-toluic acid were conducted within the preferred and general conditions of catalyst component concentrations, respectively, of the present invention. There are tabulated for the two oxidations all the pertinent conditions with respect to feed components, reaction operating conditions and the composition of the resulting oxidation products' (water-free) components on a weight percent. In said table "mga" is used to designate milligram atom, "gm To/A" is used to designate gram mole toluic acid and "IA/TA" is used to designate the sum of, respectively, isophthalic acid and terephthalic acid which are impurities resulting from m- and p-toluic acid impurities in the o-toluic acid feed.

The purpose of the presentation of the two o-toluic acid oxidations is to indicate, on a somewhat ideal basis, the composition of the final product as a standard for comparing the reaction products obtained from the oxidation of o-xylene.

TABLE I

| Conditions: | (4942-126) | (3101-132) |
|---|---|---|
| Feed: | | |
| o-Toluic Acid, gmol. | 5.0 | 3.67 |
| Co, mga/gm To/A | 1.0 | 13 |
| Mn, mga/gm To/A | 2.0 | 6.5 |
| Br, mga/gm To/A | 3.0 | 19 |
| Water, g | 25 | 0 |
| Air Rate, ml/min/gm To/A | 1000 | 1650 |
| Gauge Pressure, kg/cm$^2$ | 28.12 | 17.58 |
| Temperature: Initial 160° C. | Range 160° to 230° C. Average 226.5° C. | Range 160° to 211° C. Average 200° C. |
| Reaction Time: | 49 minutes | 90 minutes |
| Reflux Partial Condenser Gas Exit Temperature: 97° C. to 100° C. | | |
| Reaction Product Composition (without water), wt. %: | | |
| Phthalic Acid | 95.6 | 96.8 |
| Benzoic Acid | 0.66 | 0.70 |
| o-Toluic Acid | 0.21 | 0.18 |
| Phthalide | 0.086 | 0.35 |
| 2-Carboxybenzaldehyde | None Detected | 0.70 |
| High Boilers | 1.98 | Not Determined |
| Mixture of IA & TA | 1.20 | None Detected |
| Acetic Acid | 0.25 | 0.25 |
| Combustion of o-toluic acid | 2.0 mole % | 0.67 mole % |

It will be noted from the data in Table I that the use of the higher concentration of components of catalysis suppress total combustion of o-toluic acid.

The following data in Table II are from ten oxidations of o-xylene conducted according to the present invention. Said data demonstrate the same trend of increasing catalyst component concentration suppressing total combustion of o-xylene. Also included for comparison are the use of benzoic acid, or o-toluic acid initially added to the feed to be oxidized in an amount above that required to solubilize the metal catalyst components to demonstrate the effect of such acids on the total combustion of o-xylene. The use of such acids is shown in a gram mole ratio. Except for the noted differences in concentration of components of catalysis expressed in milligram atom per gram mole of xylene (mga/gmx) and the use or nonuse of such acids initially, the ten oxidations of 5.0 gram moles xylene (gmx) were conducted under substantially identical operating conditions. However, since all ten of the oxidations were terminated at the same 18 vol. % oxygen in the exhaust from the total condenser, the duration (time) of the reactions did vary with the change in concentration of components of catalysis.

TABLE II

| Example No. | 1 | 2 | 3 | 4 | 5 | 6 | 7 | 8 | 9 | 10 |
|---|---|---|---|---|---|---|---|---|---|---|
| Feed: | | | | | | | | | | |
| o-Xylene, gm | 5 | 5 | 5 | 5 | 5 | 5 | 5 | 5 | 5 | 5 |
| Co, mga/gmx | 9.5 | 7.0 | 4.5 | 1.0 | 9.5 | 4.5 | 1.0 | 1.0 | 1.0 | 0.75 |
| Mn, Mga/gmx | 4.75 | 14.0 | 9.0 | 2.0 | 4.75 | 2.75 | 2.0 | 2.0 | 2.0 | 1.5 |
| Br, mga/gmx | 14.25 | 21.0 | 13.5 | 3.0 | 14.25 | 7.25 | 3.0 | 3.0 | 3.0 | 2.25 |
| o-Toluic Acid, gm/gmx | 0.03 | 0.03 | 0.03 | 0.03 | 0 | 0 | 0 | 0.15 | 0 | 0 |
| Benzoic Acid, gm/gmx | 0 | 0 | 0 | 0 | 0.16 | 0.16 | 0.16 | 0 | 0.16 | 0.16 |
| Water, wt. % | 3 | 3 | 3 | 2 | 3 | 3 | 2 | 2 | 2 | 2 |
| Reaction Time, Min. | 61 | 73 | 86 | 101 | 64 | 66 | 68 | 90 | 86 | 85 |
| Results: | | | | | | | | | | |
| Xylene Combustion, Mole % | 4.4 | 5.8 | 6.8 | 8.8 | 2.4 | 5.2 | 6.4 | 7.8 | 6.9 | 7.2 |

It will be particularly noted that the use of as little as 0.15 to 0.16 gram mole of benzoic acid or o-toluic acid per gram mole of o-xylene will suppress total combustion at extremely low concentrations of catalyst components (Examples 7-10) down to a total combustion otherwise achieved at more than 4 times the catalyst component concentration (Example 3). It will further be noted that preference for the use of benzoic acid over o-toluic acid is supported by technical effect. For example, the use of 0.16 gram mole of benzoic acid (Examples 7 and 9) was more effective for suppressing total combustion than the use of 0.15 gram mole of o-toluic acid (Example 8), both per gram mole of o-xylene, at otherwise equivalent reaction conditions. Such superiority of benzoic acid over o-toluic acid is not due solely to the fact that the o-toluic acid unlike benzoic acid is further oxidized to o-phthalic acid and thus becomes unavailable to provide the total combustion suppressing function. By comparing Examples 2 and 8 (virtually no added v added toluic acid) it will be seen that indeed the added o-toluic acid does suppress total combustion. Such effect of added o-toluic acid v its almost non-addition (none added over amount to solubilize catalyst metals in xylene) is rather unusual because o-toluic acid is one of the natural intermediate partial oxidation products in the oxidative conversion of o-xylene to o-phthalic acid.

As previously stated the lower suitable cobalt catalyst to o-xylene concentration is 0.75 mga Co/gmx in the preferred component mga ratio of 1.0 Co:0.5 to 2.0 Mn:2 to 3 Br. Such suitability is based on activity of catalysis and total combustion as well as yield of o-phthalic acid and extent of o-xylene conversion. It was also stated that for suitable use of cobalt below 0.75 mga down to 0.3 mga/gmx there is also used a mga amount of zirconium so that the sum of zirconium and cobalt is in the range of 0.5 to 0.75 mga/gmx. Such lower suitable limit of 0.75 mga Co/gmx and the catalysis enhancing effect of zirconium are shown in Table III below presenting data from a number of o-xylene oxidation conducted according to the present invention under, except for the differences reported, identical conditions of operation.

TABLE III

| Example No. | 10 | 11 | 12 | A | B | 13 |
|---|---|---|---|---|---|---|
| Feed: | | | | | | |
| o-Xylene, gm | 5 | 5 | 5 | 5 | 5 | 5 |
| Benzoic Acid, gm/gmx | 0.16 | 0.16 | 0.16 | 0.16 | 0.16 | 0.16 |
| Co, mga/gmx | 0.75 | 0.75 | 0.35 | 0.5 | 0.375 | 0.24 |
| Mn, mga/gmx | 1.5 | 0.75 | 1.0 | 2 | 0.75 | 0.60 |
| Br mga/gmx | 2.25 | 1.125 | 1.5 | 1.5 | 1.125 | 0.90 |
| Zr, mga/gmx | 0 | 0 | 0.15 | 0 | 0 | 0.06 |
| Water, wt. % | 2 | 2 | 2 | 2 | 2 | 2 |
| Average Temperature, °C. | 227 | 227 | 227 | 227 | 224 | 227 |
| Gauge Pressure, kg/cm$^2$ | 28 | 28 | 28 | 28 | 28 | 28 |
| Reaction time to 18% O$_2$ exhaust, min. | 85 | 91 | 74 | 93 | 27 | 82 |
| o-Phthalic Acid Yield, mole % | 69.3 | 55.7 | 84.6 | 59.9 | 4.4 | 72.6 |
| o-Xylene in Reaction Product, mole % | 0.17 | 0 | 0.76 | 0.07 | 24.6 | 1.02 |
| Total combustion of xylene, mole % | 7.2 | 7.2 | 9.1 | 7.8 | 2.1 | 10 |

The reactions of comparative Examples A and B are not suitably complete and have unattractive yields of o-phthalic acids. The reaction of Example 11 is sluggish because it has insufficient bromine. Examples 12 and 13 show the unique yield and oxidation rate improving effects brought about by a small amount of zirconium which is known to have no catalytic activity but at the sacrifice of a substantially larger total combustion of o-xylene.

In the practice of the present invention we have stated that the gram atom ratio of bromine to total metals should not exceed 2:1. A series of oxidations of o-xylene under, except for differences noted, identical conditions within the practice of this invention were conducted wherein the effect of the Br: total metal gram atom ratio was varied. The results from said series of reactions are shown in Table IV below. Examples C-F are comparative examples and are not part of the present invention.

TABLE IV

| Example | No. 15 | C | D | E | F |
|---|---|---|---|---|---|
| Feed: | | | | | |
| o-Xylene, gm | 5 | 5 | 5 | 5 | 5 |
| Co, mga/gmx | 1.0 | 1.0 | 1.0 | 1.0 | 1.0 |
| Mn, mga/gmx | 2.0 | 2.0 | 2.0 | 2.0 | 2.0 |
| Br, mga/gmx | 3.0 | 4.0 | 6.0 | 12.0 | 12.0 |
| Benzoic Acid, gm/gmx | 0.16 | 0.16 | 0.16 | 0.16 | 0.15* |
| Water, wt. % | 2 | 2 | 2 | 2 | 2 |
| Average Temperature, °C. | 227 | 227 | 226 | 215 | 227 |
| Gauge Pressure, kg/cm$^2$ | 28 | 28 | 28 | 28 | 28 |
| Reaction time to 18% O$_2$ in exhaust, min. | 68 | 90 | 90 | 31 | 31 |
| Xylene total combustion, mole % | 6.4 | 7.5 | 5.7 | 2.4 | 2.5 |
| o-Phthalic Acid Yield, mole % | 81.4 | 54.6 | 50.3 | 3.97 | 4.49 |
| Intermediate Precursors, mole % | 0.013 | 25.3 | 36.3 | 31.7 | 41.9 |

*o-Toluic Acid used to replace benzoic acid.

In Table V to follow, there are described five additional o-xylene oxidations conducted batchwise within the conditions of the present invention together with the characterization of the reaction product components, less water and added benzoic acid, on a weight percent basis.

TABLE V

| Example No. | 16 | 17 | 18 | 19 | 20 |
|---|---|---|---|---|---|
| Feed: | | | | | |
| o-Xylene, gm | 5 | 5.0 | 5 | 5 | 5 |
| Co, mga/gmx | 0.75 | 1.0 | 9.5 | 1.0 | 1.0 |
| Mn, mga/gmx | 1.50 | 2.0 | 4.75 | 2.0 | 2.0 |
| Br, mga/gmx | 2.25 | 3.0 | 13.25 | 3.0 | 3.0 |
| Benzoic Acid, gm/gmx | 0.16 | 0 | 0 | 0.08 | 0 |
| Toluic Acid, gm/gmx | 0 | 0.15 | 0.03 | 0 | 0 |
| Water, wt. % | 2 | 3 | 3 | 2 | 2 |
| Initiation Temperature, °C. | 160 | 160 | 160 | 160 | 160 |
| Temperature Range, 160° to | 228 | 231 | 230 | 207 | 220 |
| Average Temperature, °C. | 227 | 227 | 227 | 205 | 219 |
| Gauge Pressure, kg/cm$^2$ | 28 | 28 | 28 | 17.6 | 24.6 |

TABLE V-continued

| Example No. | 16 | 17 | 18 | 19 | 20 |
|---|---|---|---|---|---|
| Time to 18% $O_2$ in exhaust, min. | 85 | 90 | 63 | 98 | 98 |
| Air rate: nl/min/gmx | | | | | |
| 0-20 min. | 5 | 5 | 5 | 2.5 | 2.5 |
| 20 min. to end | 5 | 5 | 5 | 4.5 | 4.5 |
| Part Condenser Exit Gas Temp., °C. | 88-93 | 88-93 | 88-93 | 87-98 | 70-105 |
| Reaction Product (water-free) | | | | | |
| o-Phthalic Acid, wt. % | 93.5 | 96.9 | 94.2 | 92.98 | 92.05 |
| Benzoic Acid, wt. % | 0.9 | 2.4 | 1.6 | 5.27 | 1.05 |
| o-Toluic Acid, wt. % | 0.6 | 0.3 | 0.2 | 0.05 | 0.07 |
| Phthalide, wt. % | 1.1 | 0.1 | 0.1 | 0.16 | 0 |
| 2-Carboxybenzaldehyde, wt. % | 0 | 0 | 0.7 | 0.03 | 0 |
| High Boilers, wt. % | 3.7 | 0.4 | 3.2 | 1.5 | 0.27 |
| o-Xylene, wt. % | 0.15 | 0 | 0 | 0 | 0 |
| Total Combustion o-xylene, mole % | 7.2 | 7.8 | 4.4 | 5.6 | 9.3 |

The following six examples in Table VI include four illustrative examples of oxidations operated within the parameters of the present invention and four comparative examples of oxidations whose only operational difference is that their water content became either above or below the suitable range of from 2 up to 7 weight percent during oxidation by the return to the oxidation zone by the reflux-partial condenser of either too much or too little water condensate.

little water (below the 2 wt. % level) also causes incomplete conversion of o-xylene to o-phthalic acid.

All of the foregoing illustrative and comparative examples have been of conventional batchwise operation. The following illustrative and comparative examples are of the modified batchwise or semi-continuous operation and comprises three modes of operation: (1) batchwise initiation of the reaction, (2) continuous introduction of xylene simultaneous with air and (3)

TABLE VI

| Example No. | 23 | G | 24 | 25 | 26 | H |
|---|---|---|---|---|---|---|
| Feed: | | | | | | |
| o-Xylene, gm | 4.72 | 4.72 | 4.72 | 4.72 | 4.72 | 5.0 |
| Co, mga/gmx | 10 | 10 | 5 | 5 | 5 | 1 |
| Mn, mga/gmx | 5 | 5 | 5 | 5 | 5 | 2 |
| Zr, mga/gmx | 0 | 0 | 5 | 5 | 5 | 0 |
| Br, mga/gmx | 15 | 15 | 15 | 15 | 15 | 3 |
| $H_2O$, wt. % | 3 | 3 | 3 | 3 | 3 | 2 |
| Initiation Temperature, °C. | 160 | 160 | 160 | 160 | 160 | 160 |
| Temperature Range from 160° C. to | 218 | 205 | 204 | 229 | 231 | 230 |
| Average Temperature, °C. | 199 | 199 | 193 | 221 | 225 | 227 |
| Gauge Pressure, kg/cm² | 17.6 | 17.6 | 17.6 | 24.6 | 28 | 28 |
| Minutes to 18 vol. % $O_2$ Exhaust | 90 | 90 | 106 | 78 | 70 | 83 |
| Partial Condenser Temp., C°. | 110 | 21 | 118 | 118 | 118 | 110 |
| Reaction Product Components: | | | | | | |
| Water, wt. % | 7.0 | 17.6 | 2.26 | 2.96 | 7.3 | 0.67 |
| o-Phthalic Acid, wt. % | 88.8 | 62.9 | 93.6 | 93.0 | 88.6 | 23.3 |
| o-Toluic Acid, wt. % | 0.5 | 4.1 | 0.2 | 0.2 | 0.2 | 46.8 |
| Phthalide wt. % | 0.2 | 9.3 | 1.5 | 0.2 | 0.02 | 15.8 |
| 2-Carboxybenzaldehyde wt. % | 0.8 | 4.9 | 0.6 | 0.7 | 0.7 | 7.3 |

Comparative Example G demonstrates that the excess water concentration in the reaction mixture causes an incomplete conversion of o-xylene. Comparative Example H whose reaction product also contained 46.1 weight % phthalic anhydride, demonstrates that too batchwise completion of the reaction by only air introduction into the liquid phase in the oxidation zone. Table VII below provides four illustrative and two comparative examples of said modified batchwise operation.

TABLE VII

| Example | 27 | 28 | 29 | 30 | J | K |
|---|---|---|---|---|---|---|
| First Batchwise Mode | | | | | | |
| Feed: | | | | | | |
| o-Xylene, gm | 5 | 5 | 5 | 5 | 5 | 5 |
| Co, mga/gmx | 10 | 10 | 10 | 10 | 10 | 10 |
| Mn, mga/gmx | 5 | 5 | 5 | 5 | 5 | 5 |
| Br, mga/gmx | 3.8 | 3.8 | 3.8 | 3.8 | 3.8 | 3.8 |
| o-Tol. Acid, mgm/gmx | 30 | 30 | 30 | 30 | 30 | 30 |
| Air rate, nl/min/gmx* | 5.0 | 5.0 | 5.0 | 5.0 | 5.0 | 5.0 |
| Continuous Mode: | | | | | | |
| o-Xylene Pumping Rate, gm/m | 0.056 | 0.056 | 0.056 | 0.056 | 0.115 | 0.057 |
| Minute Pump Started | 5 | 30 | 40 | 48 | 48 | 50 |
| Minutes of Pumping | 44 | 45 | 45 | 44 | 22 | 22 |
| Second Batchwise Mode: | | | | | | |
| Minutes to 18 vol. % $O_2$ Exhaust | 31 | 20 | 15 | 13 | 3 | 0 |
| Total Reaction Time, min. | 80 | 95 | 100 | 105 | 73 | 72 |
| Operating Temperature °C. | | | | | | |
| Initiation | 160 | 160 | 160 | 160 | 160 | 160 |
| Maximum | 227 | 230 | 227 | 227 | 227 | 227 |
| Average | 221 | 227 | 227 | 227 | 222 | 226 |

TABLE VII-continued

| Example | 27 | 28 | 29 | 30 | J | K |
|---|---|---|---|---|---|---|
| Gauge Pressure, kg/cm$^2$ | 28 | 28 | 28 | 28 | 28 | 28 |
| Reflux Condenser Outlet Gas, °C. | 115 | 118 | 118 | 115 | 110 | 112 |
| Reaction Product: | | | | | | |
| o-Phthalic Acid, wt. % | 91.3 | 91.9 | 89.1 | 90 | 54.6 | 71.6 |
| o-Toluic Acid, wt. % | 0.22 | 0.24 | 0.13 | 0.23 | 9.1 | 4.4 |
| Phthalide, wt. % | 0.05 | 0.10 | 0.05 | 0.47 | 8.8 | 6.3 |
| 2-Carboxybenzaldehyde, wt. % | 0.80 | 0.90 | 1.0 | 0.94 | 5.4 | 3.0 |
| Water, wt. % | 6.3 | 4.9 | 7.5 | 4.6 | 13.4 | 9.4 |
| o-Xylene Total Combustion Mole % | 7.0 | 7.2 | 9.7 | 8.7 | 5.8 | 5.8 |

*Based on 5.0 gram moles o-xylene initially charged.

The successful results of the semi-continuous oxidations of Examples 27 to 30 establish that the differences between the present inventive process and the unsuccessful single step oxidation of British Pat. No. 856,245 are differences in kind. Further the high o-phthalic acid content of the reaction products of Examples 27 to 30 are indeed unexpected from the teachings in said British Patent that upon addition of fresh o-xylene to the partial oxidation products of o-xylene there would be little or no useful oxidation but rather only tarry products would be formed for a short time and then oxygen consumption would abruptly cease.

Also from the comparative Examples J and K it will be noted that accumulation in the reaction mixture of water in excess of 7 wt. %, as in the simple batchwise operation, causes the oxidation to cease before a suitably complete o-xylene oxidation (high o-phthalic acid content and low precursors content in the reaction mixture) can occur.

Part of the o-xylene oxidized according to the process of the present invention goes to high boiling products rather than to o-phthalic acid or its precursor intermediate oxidation products: o-toluic acid, phthalide, and 2-carboxybenzaldehyde. Such high boiling products, having normal (at 760 mm Hg) boiling temperatures above 295° C. and molecular weights above 166. The major amount (70-80%) of the identified high boiling products include dimethylcarboxybenzophenone, methyldicarboxybenzophenone, tricarboxybenzophenone, di-carboxybenzocourmarine, 1,3-indanedione, tricarboxytriphenyl, and biscarboxyanthraquinone. Minor to trace amounts of impurities include ester compounds such as o-methylbenzyl alcohol esters of o-toluic acid, benzoic acid, o-phthalic acid, and 2-carboxybenzaldehyde.

The invention claimed is:

1. For the process of catalytically oxidizing o-xylene with air at a temperature of at least 150° C. in the absence of a solvent in a stirred oxidation zone under pressure to maintain at least the o-xylene in the liquid phase wherein catalysis is provided by manganese and/or cobalt with or without a source of bromine and the mode of operation comprises either single step batchwise operation or batchwise operation modified by substituting continuous supply of at least a portion of the o-xylene simultaneously with the addition of air into the oxidation zone in place of charging to said zone all of the xylene prior to such addition of air; the improvement for such process of oxidizing o-xylene comprising, conducting said oxidation at a temperature in the range of from 150° C. up to 235° C., in the presence of free water in an amount of from at least 2 percent up to 7 weight percent of the reaction mixture, under a gauge pressure of from 17.6 up to at least 28 kg/cm$^2$ to maintain the reaction mixture components in the liquid phase and the xylene oxidation product as liquid o-phthalic acid and based on one gram mole of o-xylene the catalysis (a) provided by at least 0.3 up to 10 milligram atoms of cobalt and from 0.2 up to 0.45 milligram atom of zirconium when said cobalt concentration is less than 0.75 milligram atom and based on such concentrations of cobalt or cobalt and zirconium from 0.5 up to 2 milligram atoms of manganese per milligram atom of cobalt or total of cobalt and zirconium and at least 0.5 but less than 2.0 milligram atoms of bromine per milligram atoms of the total of manganese and cobalt or manganese, cobalt and zirconium, and (b) initially solubilized by an amount of equivalents of o-toluic acid or benzoic acid equal to the equivalents of said metals cobalt, manganese and zirconium.

2. The process of claim 1 wherein the oxidation is initiated at a temperature of from 150° to 160° C. and conducted at an average temperature of from 205° up to 227° C. at a gauge pressure of 20 kg/cm$^2$, in the presence of from 3 to 5 weight percent free liquid water, under a gauge pressure of 28 kg/cm$^2$, and in the presence of catalysis provided by from 0.75 up to 1.0 milligram atom of cobalt, from 1.5 up to 2 milligram atoms of manganese and from 2.25 up to 3.0 milligram atoms of bromine per gram mole of o-xylene.

3. The process of claim 2 wherein the total combustion of o-xylene to water and oxides of carbon is suppressed by conducting the oxidation in the presence of from 0.1 up to 0.2 gram mole of benzoic acid or o-toluic acid per gram mole of o-xylene.

4. The process of claim 3 wherein benzoic acid is used for both the initial solubilizing of the metal components of catalysis and for suppression of said total o-xylene combustion.

5. The process of claim 4 conducted by the modified batchwise oxidation wherein following the continuous mode of charging o-xylene the mode of only introducing air is conducted for from 13 up to 30 minutes.

* * * * *

UNITED STATES PATENT OFFICE
CERTIFICATE OF CORRECTION

Patent No. 4,299,977　　　　　　　　　　Dated November 10, 1981

Inventor(s) George E. Kuhlmann and Alan G. Bemis

It is certified that error appears in the above-identified patent and that said Letters Patent are hereby corrected as shown below:

Patent reads:

| Col. | Line | |
|---|---|---|
| Abstract | 15 | "to o-phthalic" should be --of o-phthalic-- |
| 1 | 20 | "amounts" should be --amount-- |
| 1 | 64 | "British Pat. No." should be --British Patent Specification No.-- |
| 2 | 5 | "is" should be --are-- |
| 2 | 66 | "cease" should be --ceases-- |
| 4 | 30 | "are" should be --is-- |
| 6 | 54 | "invention" should be --inventive-- |
| 7 | 32 | "supresses" should be --suppresses-- |
| 8 | 31 | "suppress" should be --suppresses-- |

UNITED STATES PATENT OFFICE
CERTIFICATE OF CORRECTION

Patent No. 4,299,977    Dated November 10, 1981

Inventor(s) George E. Kuhlmann and Alan G. Bemis

It is certified that error appears in the above-identified patent and that said Letters Patent are hereby corrected as shown below:

| Patent reads: Col. | Line | |
|---|---|---|
| 8 | Table II Line 5 | "Mn, Mga/gmx" should be --Mn, mga/gmx-- |
| 12 | 23 | "comprises" should be --comprise-- |
| 13 | 16 | "British Pat. No." should be --British Patent Specification No.-- |
| 14 | 14-15 | "comprising, conducting said oxidation" should be --comprising initiating the oxidation-- |
| 14 | 19 | "17.6 up" should be --17.6 kg/cm$^2$ up-- |
| 14 | 23 | "by at least" should be --provided by the components of at least-- |

UNITED STATES PATENT OFFICE
CERTIFICATE OF CORRECTION

Patent No. 4,299,977                         Dated   November 10, 1981

Inventor(s)   George E. Kuhlmann and Alan G. Bemis

It is certified that error appears in the above-identified patent and that said Letters Patent are hereby corrected as shown below:

Patent reads:

| Col. | Line | |
|------|------|---|
| 14   | 35   | "zirconium." should be --zirconium; and continuing the conduct of the initiated oxidation of liquid o-xylene at said temperature in the range of from 150°C up to 235°C, in the presence of said free water concentration of from 2 up to 7 weight percent, under said gauge pressure of from 17.6 up to 28 kg/cm$^2$, and in the presence of said concentration of components of catalysis.-- |

Signed and Sealed this

Thirteenth Day of April 1982

[SEAL]

Attest:

GERALD J. MOSSINGHOFF

*Attesting Officer*          *Commissioner of Patents and Trademarks*